United States Patent [19]
Gossens et al.

[11] Patent Number: 5,011,480
[45] Date of Patent: * Apr. 30, 1991

[54] ABSORBENT ARTICLE HAVING A NONWOVEN FRICTIONAL SURFACE FOR HOLDING THE ARTICLE IN PLACE AND A METHOD OF USE

[75] Inventors: Anthonette A. Gossens, Neenah, Wis.; Mary L. Schwer, New Milford, Conn.

[73] Assignee: Kimberly-Clark Corporation, Neenah, Wis.

[*] Notice: The portion of the term of this patent subsequent to Feb. 7, 2006 has been disclaimed.

[21] Appl. No.: 358,320

[22] Filed: May 25, 1989

Related U.S. Application Data

[63] Continuation-in-part of Ser. No. 134,426, Dec. 17, 1987, abandoned.

[51] Int. Cl.$^5$ ............................................. A61F 15/16
[52] U.S. Cl. ................................. 604/385.1; 604/306
[58] Field of Search .................. 604/385.1, 385.2, 358, 604/386, 387, 389, 375, 376

[56] References Cited

U.S. PATENT DOCUMENTS

| | | | |
|---|---|---|---|
| 3,888,255 | 6/1975 | Shah et al. | 604/366 |
| 4,536,433 | 8/1985 | Sagi et al. | 604/358 |
| 4,655,760 | 4/1987 | Morman et al. | 604/385 A |
| 4,657,802 | 4/1987 | Morman | 428/152 |
| 4,663,220 | 5/1987 | Wisneski et al. | 428/221 |
| 4,720,415 | 1/1988 | van der Wielen et al. | 428/152 |
| 4,834,739 | 5/1989 | Linker, III et al. | 604/385.1 |

FOREIGN PATENT DOCUMENTS

| | | |
|---|---|---|
| 0213642 | 9/1986 | European Pat. Off. . |
| 0215408 | 9/1986 | European Pat. Off. . |
| 1398011 | 6/1972 | United Kingdom . |
| 2114895 | 2/1983 | United Kingdom . |

*Primary Examiner*—Randall L. Green
*Assistant Examiner*—K. Reichle
*Attorney, Agent, or Firm*—Thomas J. Conelly

[57] ABSTRACT

An absorbent article is disclosed which contains an absorbent positioned between a fluid permeable cover and a fluid-impermeable baffle. The baffle can be either a nonwoven web or have a nonwoven web secured to it. The nonwoven web hs a high coefficient of friction so as to hold the absorbent article stationary relative to an adjacent undergarment and thereby retain the absorbent article in a comfortable position relative to the body of the user. The nonwoven web is a dry, soft, non-tacky, fibrous material which can have an elastomeric component. The nonwoven web can partially or totally cover the exterior surface of the absorbent article which is away from the body of the user.

27 Claims, 6 Drawing Sheets

ABSORBENT ARTICLE HAVING A NONWOVEN FRICTIONAL SURFACE FOR HOLDING THE ARTICLE IN PLACE AND A METHOD OF USE

This application is a continuation-in-part application of U.S. Ser. No. 07/134,426 filed Dec. 17, 1987, to inventors A. A. Gossens and M. L. Schwer. This patent application entitled "External Feminine Protection Device With Elastomeric Nonwoven for Holding the Device in Place" was abandoned on July 12, 1989.

FIELD OF THE INVENTION

This invention relates to an absorbent article having a nonwoven frictional surface for holding the article stationary relative to an adjacent undergarment and a method of use.

BACKGROUND OF THE INVENTION

Currently, there are a number of external absorption articles, such as feminine pads, panty liners, incontinent garments, etc., which are designed to absorb and retain a variety of body fluids. catamenial devices in particular are designed to absorb menstrual fluids, urine and other body fluids discharged from the vaginal cavity. Such devices are designed to be positioned externally of the body and adjacent to the perineum of a user.

A majority of catamenial devices are normally held in position by the use of an adhesive located on the backside of the pad which physically attaches to an adjacent undergarment. The use of pressure sensitive or hot melt adhesives have several disadvantages. First, the adhesive may stick too firmly to the undergarment and may make removal difficult. This becomes especially annoying when the user finds that the absorbent pad is not in the correct position and must be moved slightly so as to be more comfortable. A second disadvantage is that the adhesive may discolor the undergarment or leave a sticky residue on it. Neither is appreciated by the end user. A third disadvantage is that when the adhesive is too strong, it may cause the absorbent pad to be torn apart at its time of removal. Since the pad has absorbed a certain quantity of fluid, the destruction of the pad upon removing it from the undergarment may cause a mess.

Along with the above mentioned disadvantages, the cost of pressure sensitive adhesives and the peel strips necessary to cover them represent a significant portion of the cost of the overall pad. Furthermore, should the user inadvertently place the pad upside down in the undergarment, the adhesive would contact the body and may cause discomfort upon removal by causing some body hairs to be removed along with it.

An alternative to the use of adhesives is belt or strap attachments which are used to hold the absorbent article in place. However, such attachment devices have been losing interest in the marketplace because they are not discrete, especially when the user wears tight fitting clothing. In addition, they are relatively difficult to adjust and attach which discourages their use, especially among older people.

Therefore, there is a need for a product which does not rely upon an adhesive to retain it in position relative to an adjacent undergarment while still maintaining its correct position relative to its placement adjacent to the body of the user.

Several attempts to provide feminine pads and other types of absorbent products with frictional surfaces have been proposed. U.S. Pat. No. 3,881,490 issued to Howard Whitehead in 1975, describes the use of a polyurethane foam laminated to the baffle material. The foam provides a high friction surface which maintains the pad in place when the pad is worn with a tight undergarment. U.S. Pat. No. 4,315,507 issued to Whitehead et al. in 1982 teaches a sanitary napkin with a heat fusible baffle having a roughened frictional surface so that the conventional adhesive could be avoided. The baffle material is described as being thermoplastic. U.S. Ser. No. 07/134,423, filed Dec. 17, 1987, assigned to Kimberly-Clark Corporation and allowed on Dec. 15, 1988, describes an external feminine protection device with skid resistant coating for holding the device in place. The pad uses a nonadhesive coating having a high coefficient of friction which can hold the pad in place either against the user's body or to an undergarment. In U.S. Pat. No. 4,490,148 issued to Bo Beckestrom in 1984, a diaper is taught which incorporates a friction increasing strip fixed to the underside baffle. The strip is intended to cooperate with the briefs which are used in a known manner to hold the diaper in place. U.S. Pat. No. 4,389,211 issued to Lenaghan in 1983, teaches a catamenia bandage wherein ELCRO ® material is applied to a foam outer sheath to retain the pad in place. U.S. Pat. No. 4,488,918 issued to J. E. Jofs teaches a method of making a film of plastic material with a non-slip surface having a high coefficient of friction. However, each of the above identified materials and products seem to suffer from some type of disadvantage. The most notable is that some require an adhesive spray or coating which may be difficult to apply uniformly to the product. Furthermore, tacky coatings and plastic films have not been readily accepted in the marketplace because they are viewed as being similar to adhesives or, especially in the case of plastic films, cause noise when the user walks or runs thereby discouraging their use.

Accordingly, there is a need for an absorbent article which uses a soft, nonwoven friction material to hold the article in place against an adjacent undergarment.

SUMMARY OF THE INVENTION

Briefly, this invention relates to an absorbent article, such as a feminine pad, panty liner, incontinent garment, etc., which is designed to absorb and retain body exudate. The absorbent article comprises an absorbent, a fluid permeable cover adjacent to one surface of the absorbent which faces the body of a user, and a fluid impermeable baffle positioned adjacent to an opposite surface of the absorbent and which faces away from the body of the user. A nonwoven web is secured to the baffle and provides a frictional surface which cooperates with an adjacent undergarment to retain the absorbent article in a desired position relative to the perineum of the user. The coefficient of friction of the nonwoven web is preferably greater than about 2 and the web should have a Sheffield smoothness rating of greater than about 400.

The general object of this invention is to provide an absorbent article which has a nonwoven web attached to the baffle which serves as a frictional surface for retaining the absorbent article in a desired position relative to an adjacent undergarment. A more specific object of this invention is to provide an absorbent article with a nonwoven elastomeric web having a Sheffield smoothness rating of greater than about 400.

Another object of this invention is to provide a feminine pad, panty liner, incontinent garment, etc., with a non-tacky, non-adhesive, non-film surface which has a sufficient coefficient of friction to retain the article relative to an adjacent undergarment.

A more specific object of this invention is to provide an absorbent article with a nonwoven frictional web attached to a fluid-impermeable baffle without the use of an adhesive.

Still further, an object of this invention is to provide a relatively inexpensive and easily to produce absorbent article having a nonwoven high frictional surface which faces away from the body of the user.

Other objects and advantages of the present invention will become more apparent to those skilled in the art in view of the following description and the accompanying drawings.

DETAILED DESCRIPTION OF THE PREFERRED EMBODIMENTS

Referring to FIGS. 1-5 an absorbent article 10, such as a feminine pad, a panty liner or an incontinent garment is shown. The absorbent article 10 includes an absorbent 12 having a first surface 14 and a second surface 16, best shown in FIG. 5. The absorbent 12 can be a cellulose fluff, coform, meltblown, woodpulp, tissue, etc., which are commonly known in the art. A bodyside fluid permeable cover 18 is positioned adjacent to the first surface 14 of the absorbent 12. The cover 18 is designed to allow body fluids, such as menstrual fluid, urine, blood, as well as various small particles of solid matter to pass therethrough and be absorbed and retained by the absorbent 12. Positioned adjacent to the second surface 16 of the absorbent 12 is a fluid-impermeable baffle 20, which is preferably constructed of a thermoplastic material. For feminine pads in particular, the baffle 20 has a configuration which is coextensive with the cover 18 and cooperates with the cover 18 to sandwich the absorbent 12 therebetween. Normally, the cover 18 is attached to the baffle 20 by a perimeter seal 22. The seal 22 can be formed just inward of the outer perimeter and can be formed by heat, ultrasonic bonding, or by the use of an adhesive.

Figure 1:
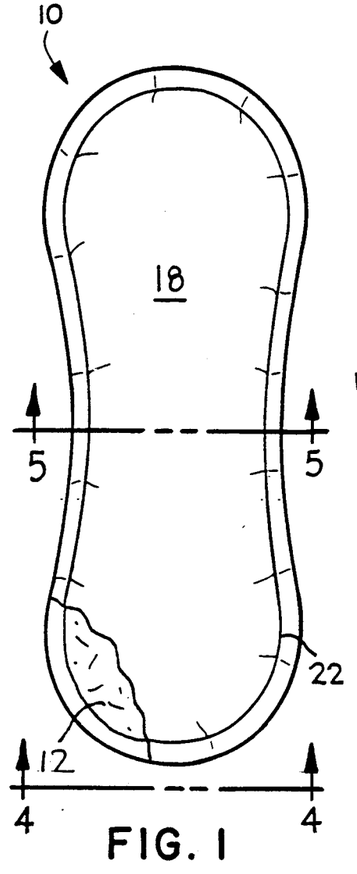
FIG. 1 is a top view of an absorbent article, such as a feminine pad, having a cut away portion showing the absorbent position beneath the bodyside cover.
Figure 2:
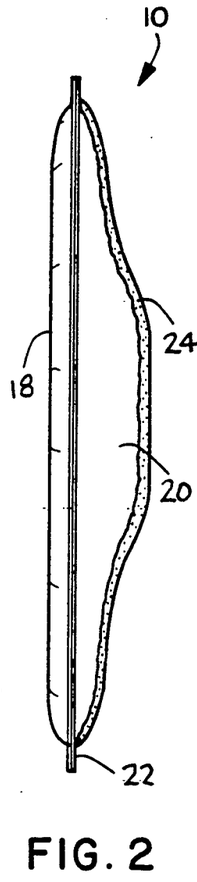
FIG. 2 is a side view of the absorbent article shown in FIG. 1.
Figure 3:
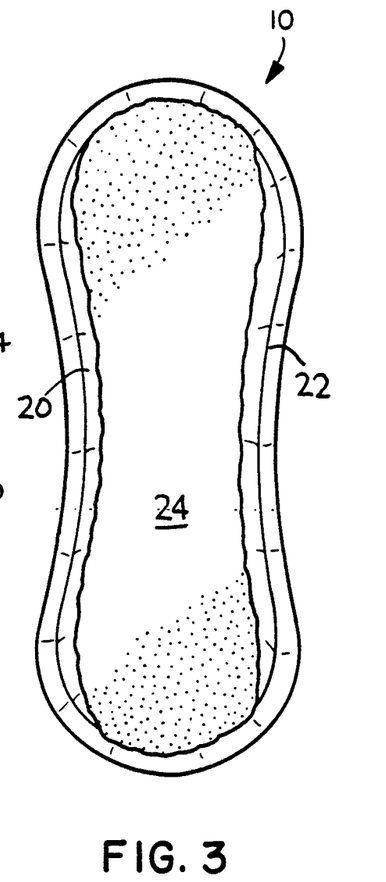
FIG. 3 is a bottom view of the absorbent article shown in FIG. 1, depicting the nonwoven web attached to the fluid-impermeable baffle.
Figure 4:
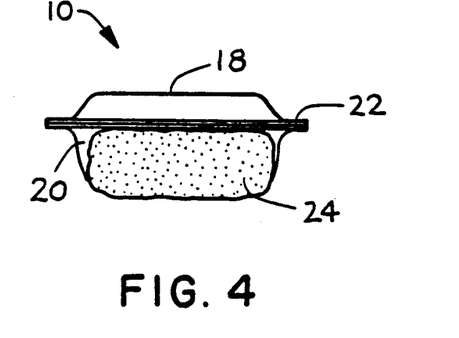
FIG. 4 is an end view of FIG. 1 taken along line 4—4.
Figure 5:
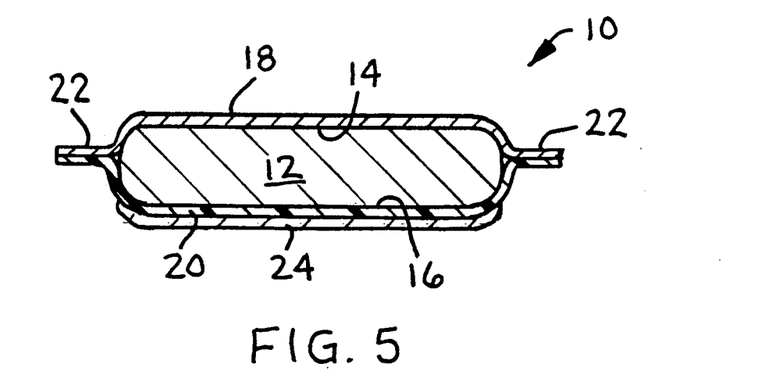
FIG. 5 is a cross-sectional view of the absorbent article shown in FIG. 1 taken along line 5—5.

A nonwoven web 24 is secured to the baffle 20, either directly or by an intermediate attachment means such as an adhesive. The nonwoven web 24 is a fibrous material which is soft, dry, and non-tacky to the touch. The nonwoven web 24 can have an elastomeric property if desired. The nonwoven web 24 has a coefficient of friction of greater than about 2 as measured by a Davis Modified Form of ASTM Test Number D-1894. The normal test calls for a sled wrapped with Naugahyde to be pulled across the test sample at 5 inches per minute. The modified test involves wrapping each sled with a test sample and pulling it across a Naugahyde sheet. Using this test, a coefficient of friction of greater than about 2 has been found to work well. The nonwoven web 24 also has a Sheffield smoothness rating of greater than about 400. The nonwoven web 24 has anti-skid properties and therefore is skid resistant and can secure the absorbent article 10 to an adjacent undergarment. The nonwoven web 24 is designed to retain the absorbent article 10 in a desired position relative to the perineum of a user. In normal use the user will place the absorbent article 10 adjacent to his or her body with the cover 18 contacting the perineum. The user will then pull an undergarment up into contact with the absorbent article 10 whereby the nonwoven web 24 will frictionally contact the undergarment and hold the absorbent article 10 stationary relative to the undergarment.

The nonwoven web 24 can be any rubbery composition containing elastomeric components such as natural rubber and isobutylene, polymerized or blended with other polymers that are provided to control the degradation, melting point and plasticity of the elastomers. The nonwoven web 24 can include microfibers comprising at least about ten percent (10%) by weight of an A—B—A' block copolymer where A and A' are each a thermoplastic end block which includes a styrenic moiety and where B is an elastomeric poly(ethylene-butalyene) midblock, and from greater than zero percent (0%) by weight, up to about ninety percent (90%) by weight of a polyolefin, which, when blended with the A—B—A' block copolymer and subjected to an effected combination of elevated temperature and pressure conditions, is adapted to be extruded, in blended form, with the A—B—A' block copolymer. The polyolefin recited above can be selected from the group consisting of polyethylene, polypropylene, polybutene, ethylene copolymers, propylene copolymers, butane copolymers and blends of at least two of the above materials. U.S. Pat. Nos. 4,663,220, 4,692,371, 4,741,949, 4,789,699, and 4,803,117 all of which are assigned to Kimberly-Clark Corporation, are incorporated by reference and made a part hereof. The above-identified patents describe extrudable compositions and method of forming such compositions especially elastomeric nonwoven webs. Such materials are useful in making the nonwoven web 24.

In addition, the nonwoven web 24 can include A—B—A' block copolymers with polybutydiene or polyacetate midblocks and polystyrene end blocks, polystyrene/polyethylenebutylene/polystyrene block copolymer resins and blends of such resins with materials to control their plasticity and degradation. It should be noted that such compositions should be readably extrudable and be easily formed into fibrous webs.

Figure 6:
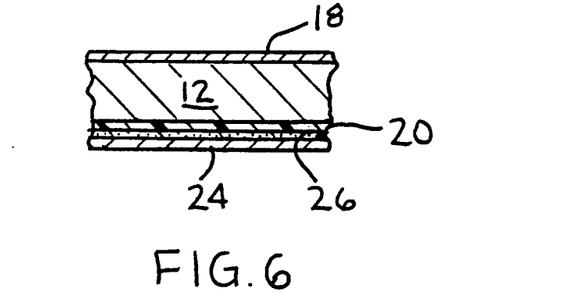
FIG. 6 is a partial schematic cross-sectional view of an absorbent article showing the nonwoven web secured to the baffle by independent attachment means.

Referring to FIGS. 5 and 6, the nonwoven web 24 can be bonded directly to the baffle 20 by the use of heat such that a physical or chemical bond is created. The nonwoven web 24 can also be secured directly to the baffle 20 by an attachment 26, such as two sided tape, glue, construction adhesive, etc. It should be noted that if a fluid-impermeable nonwoven web 24 is utilized, it is possible to use a fluid permeable material, such as gauze or tissue for the baffle. The nonwoven web 24 will then serve as the fluid-impermeable barrier member. The nonwoven web 24, when attached to a fluid-impermeable baffle 20, can partially or totally cover the exterior surface of the baffle 20. In addition, the nonwoven web 24 can be located on a portion of the bodyside cover 18 if desired, so as to retain the absorbent article 10 in position relative to the user's body. However, because most consumers do not want a frictional surface in contact with their body, it is preferred to place the nonwoven web 24 only on the surface which is positioned away from the body of the user.

Figure 7:
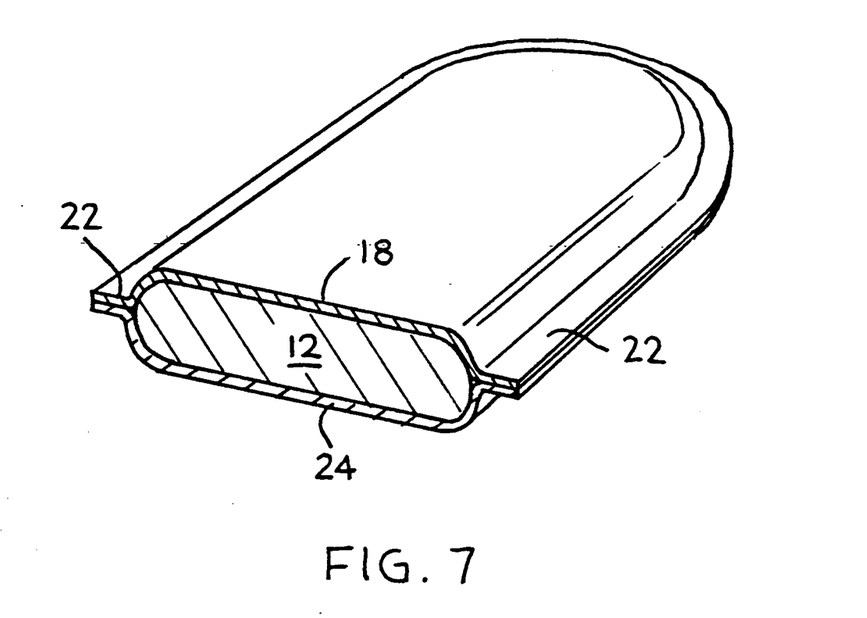
FIG. 7 is a partial perspective view of an alternative absorbent article wherein the nonwoven web is secured directly to the absorbent and is sealed about the perimeter of the article to a coextensive cover.

Referring to FIG. 7, an alternative embodiment is shown wherein the nonwoven web 24 is secured directly to the absorbent 12 and is sealed about its outer perimeter at 22 to the cover 18. In this configuration, the cost of a baffle layer is eliminated completely and the nonwoven web 24 would have to be fluid-impermeable and nonporous. It should be noted that it could be possible to form the nonwoven web 24 such that its exterior surface has a high coefficient of friction while its interior surface has other properties which allow it to be readily bonded to an absorbent or baffle material.

Figure 8:
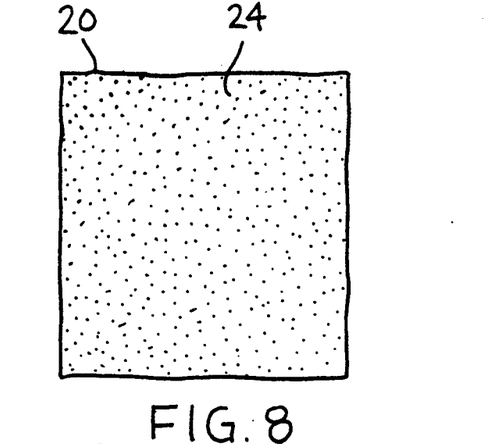
FIG. 8 is a rectangular section of a baffle material completely covered by a fluid-impermeable nonwoven web.
Figure 9:
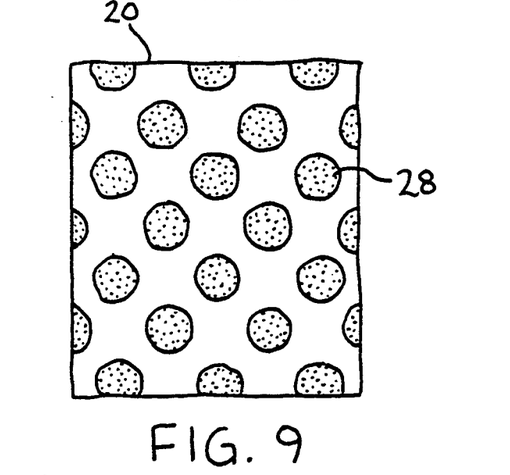
FIG. 9 is a rectangular section of a baffle material having a nonwoven material sprayed on to discrete areas.
Figure 10:
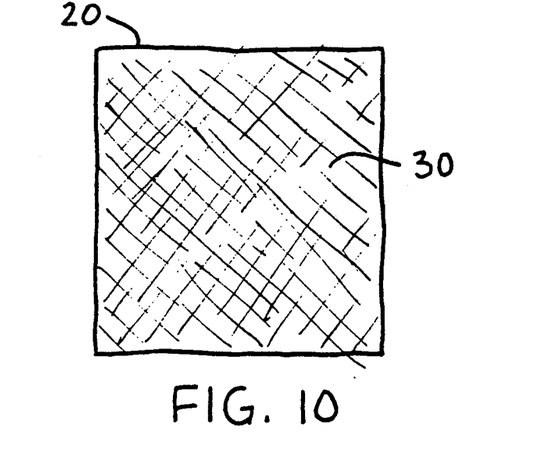
FIG. 10 is a rectangular section of a baffle material having a porous, nonwoven web secured thereto.

Referring to FIGS. 8-10, three alternative methods of attaching a nonwoven web to a baffle are shown. In FIG. 8, the nonwoven web 24 is attached to the baffle 20 so as to cover the complete exterior surface. The thickness of the nonwoven web 24 would be approximately uniform throughout and would have a nonporous feature. In FIG. 9, a nonwoven web 28, having a liquid consistency, is sprayed onto portions of the baffle 20 so as to cover only certain areas. In this embodiment, the nonwoven web 28 would be sprayed either at room temperature or at an elevated temperature onto the baffle 20 at desired locations where needed so as to allow the absorbent article to be retained in place. In FIG. 10, a nonwoven web 30, having a porous structure, is shown secured to the baffle 20. The nonwoven web 30 would have to be applied to a fluid-impermeable baffle 20 which would act as the fluid barrier. The nonwoven web 30 would provide the frictional contact so as to adhere the absorbent article to an undergarment. By using a porous web, one may be able to reduce the cost of the nonwoven material.

Figure 11:
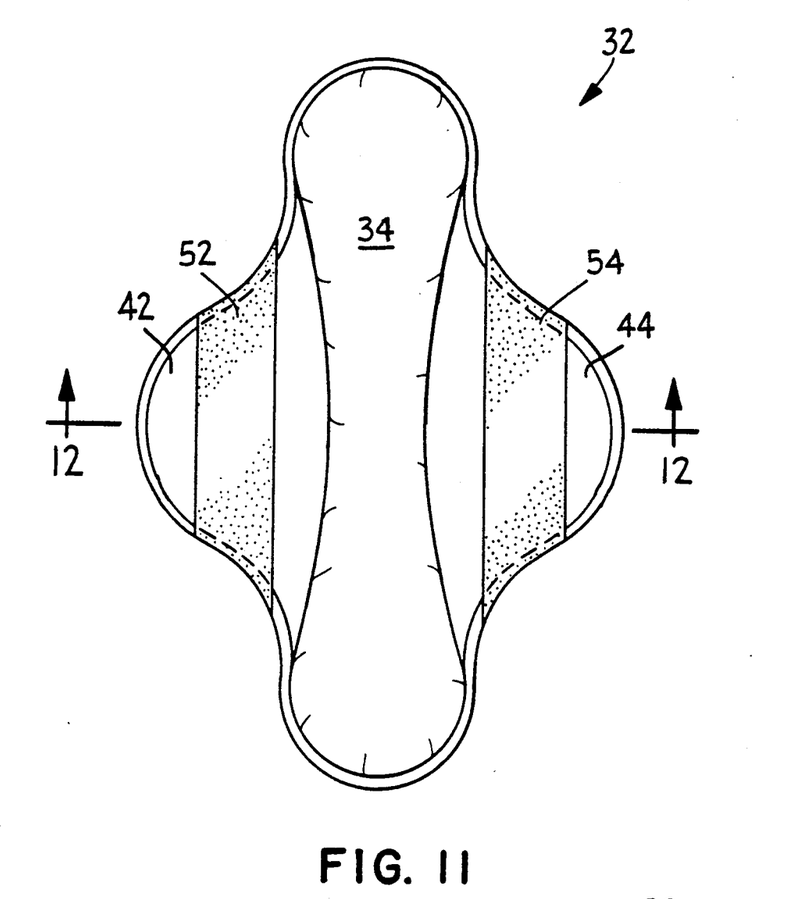
FIG. 11 is an alternative embodiment of a feminine pad having a pair of outwardly extending wings with a nonwoven web secured to a portion of each of said wings.
Figure 12:
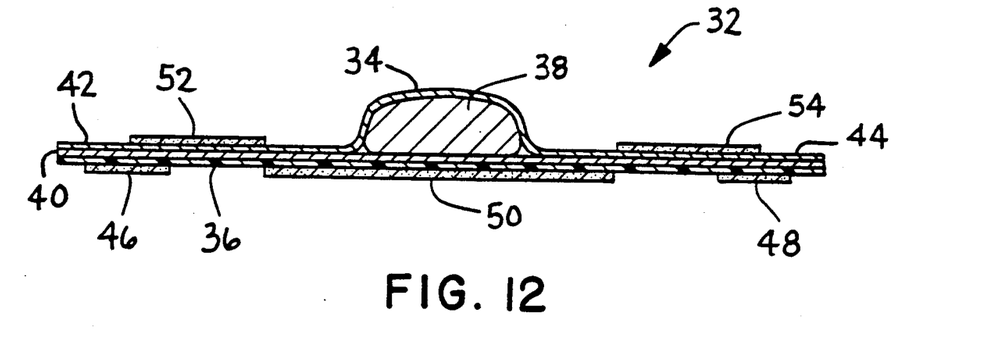
FIG. 12 is a cross-sectional view of FIG. 11 taken along line 12—12.
Figure 15:
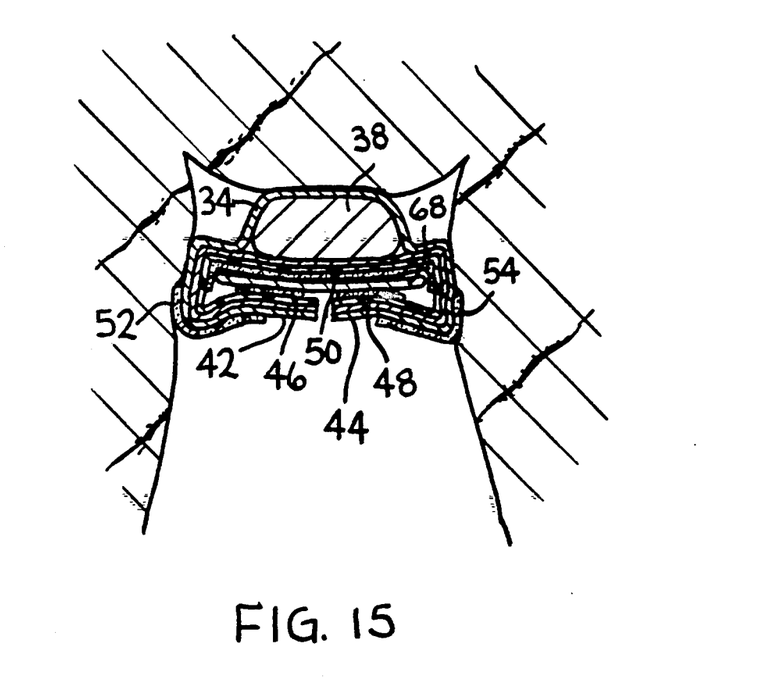
FIG. 15 is a schematic view of the feminine pad shown in FIGS. 11 and 12 as it is wrapped around the crotch portion of an undergarment while in use.

Referring to FIGS. 11, 12 and 15, a feminine pad 32 is shown having a fluid permeable bodyside cover 34, a fluid-impermeable baffle 36 and first and second adsorbents 38 and 40, respectively, positioned therebetween. The pad 32 has a pair of outwardly extending wings 42 and 44, which consist of coextensive material including the cover 34, the second absorbent 40 and the baffle 36. Attached to a lower surface of the wings 42 and 44, are garment adhesive strips 46 and 48, respectively. The wings 42 and 44 are designed to be folded under the crotch portion of an undergarment and be secured to the external lower surface of the undergarment by the adhesive strips 46 and 48. The pad 32 also contains a nonwoven web 50 secured to a portion of the baffle 36 approximately along the longitudinal central axis. The nonwoven web 50 would contact the inside surface of the crotch portion of an adjacent undergarment and provide frictional contact to retain the pad 32 in a desired position. In addition, the pad 32 can optionally have nonwoven web segments 52 and 54 secured to a top surface of each of the wings 42 and 44, respectively. The nonwoven web segments 52 and 54 are on the bodyside surface of the pad 32 and will contact the body of the wearer approximate the groin, see FIG. 15. The nonwoven web segments 52 and 54 will increase the skid resistance of the pad 32 and prevent movement thereof. It should be noted that feminine pads, panty liners, and incontinent garments come in various sizes and shapes and vary in thickness. Because of this, it may be desirous to place the nonwoven web on only a small portion of the underside of the product or, to place the nonwoven web on both sides of the product if additional holding power is needed.

Figure 13:
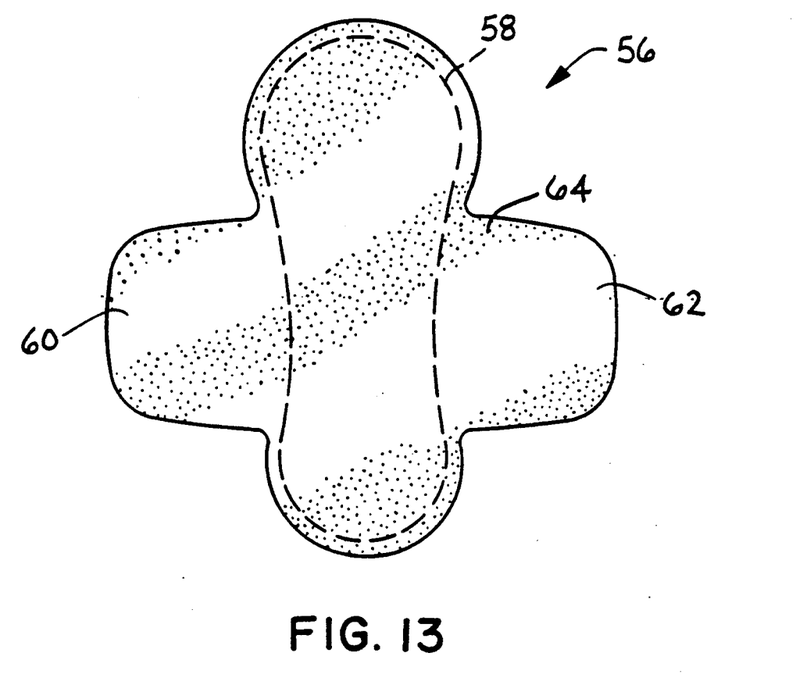
FIG. 13 is a bottom view of another embodiment of a feminine pad having a pair of outwardly extending wings wherein the nonwoven web completely covers the bottom surface of the pad.

Referring to FIG. 13, a feminine pad 56 is shown having an hourglass shape absorbent structure 58, the outline of which is indicated by a dotted line. The feminine pad 56 also has a pair of outwardly extending wings 60 and 62. The entire lower surface of the pad 56, including the wings 62 and 64, is covered by a nonwoven web 64 which will provide frictional contact with both the adjacent undergarment and the person's body.

Figure 14:
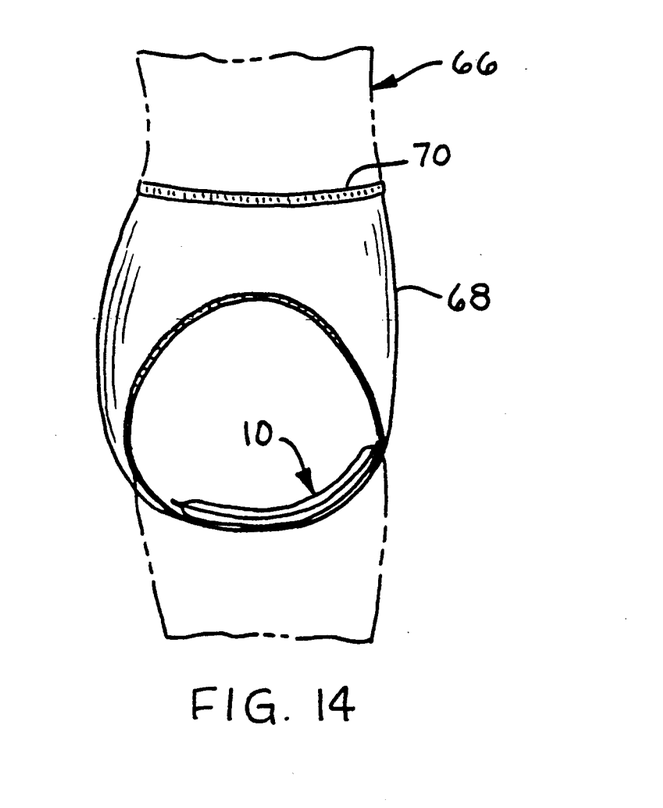
FIG. 14 is a schematic view of a human torso having an absorbent article positioned adjacent the perineum and being held in place by the frictional contact of the nonwoven web against an adjacent undergarment.

Referring to FIG. 14, an outline of a human body 66 is shown having the absorbent article 10 positioned adjacent to the perineum. The absorbent article 10 is frictionally held in contact to an undergarment 68 which is pulled up and secured around the waist, such as by an elastic waistband 70. The method of retaining the absorbent article 10 in a desired position relative to a user's perineum involves placing the absorbent article 10 adjacent to the body so that it covers the perineum. The user will then pull the undergarment 68 up such that it contacts the absorbent article 10 and the frictional surface of the nonwoven web will cause the absorbent article 10 to be held stationary relative to the undergarment 68. If the wearer should find that the absorbent article 10 is not correctly positioned, the undergarment can be pulled down and the absorbent article 10 can be repositioned. The undergarment is then pulled back up to the waist. The nonwoven web provides frictional contact so as to hold the absorbent article stationary relative to the undergarment, but also provides an easy means for repositioning the article once the pressure securing the absorbent article 10 to the undergarment is removed. Alternatively, the user can position the absorbent article 10 on the inside of the undergarment so that the frictional, nonwoven surface will retain it in place. Then the undergarment is pulled up to the waist. The nonwoven web has an advantage over adhesives, since it is dry and non-tacky and therefore will not leave a sticky residue on the undergarment after the pad has been worn and discarded.

The nonwoven web 24 has been described as being of conventional feminine pads, panty liners, and incontinent garments, but could also be utilized on other products designed for labial dispositions such as is taught in U.S. Pat. No. 4,673,403 issued to Lassen et al. The nonwoven web 24 could also be placed on the ends or edges of a product near the ends or edges to hold it stationary.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An absorbent article comprising first and second members cooperating to enclose an absorbent, one of said members being a fibrous, nonwoven web having an external frictional surface with a Sheffield smoothness rating of greater than 400, said frictional surface assisting in retaining said absorbent article in a desired position.

2. The absorbent article of claim 1 wherein said first member is a fluid-permeable cover and said second member is a fluid-impermeable baffle, said cover and baffle being coextensive and attached to each other about the perimeter thereof.

3. The absorbent article of claim 1 wherein said nonwoven web has a dry, non-tacky feel and a coefficient of friction of greater than about 2.

4. An absorbent article designed to contact a human body and be retained in place by an undergarment, said article comprising:
    (a) first and second members cooperating to enclose an absorbent; and
    (b) nonwoven means for retaining said absorbent article in frictional contact with said undergarment, said nonwoven means being secured to one of said members and having a frictional surface with a Sheffield smoothness rating of greater than 400.

5. The absorbent article of claim 4 wherein said nonwoven means is a fibrous web.

6. The absorbent article of claim 5 wherein said fibrous web has a coefficient of friction of greater than about 2.

7. The absorbent article of claim 5 wherein said fibrous web is fluid-impermeable.

8. The absorbent article of claim 4 wherein said nonwoven means is secured to said first and second members.

9. An absorbent article designed to contact a human body and be retained in place by an undergarment, said article comprising:
    (a) a fluid-permeable cover;
    (b) a fluid-impermeable baffle;
    (c) an absorbent enclosed by said cover and said baffle; and
    (d) nonwoven means for retaining said absorbent article in frictional contact with said undergarment, said nonwoven means being secured to said baffle and having an external frictional surface with a Sheffield smoothness rating of greater than 400.

10. The absorbent article of claim 9 wherein said nonwoven means is a fibrous web having a coefficient of friction of greater than about 2.

11. The absorbent article of claim 10 wherein said fibrous web is secured to said baffle by an adhesive.

12. The absorbent article of claim 9 wherein said nonwoven means partially covers said baffle.

13. The absorbent article of claim 9 wherein said nonwoven means totally covers said baffle.

14. An absorbent article designed to contact a human body and be retained in place by an undergarment, said article comprising:
    (a) an absorbent having first and second surfaces;
    (b) a fluid-permeable cover positioned adjacent to said first surface of said absorbent;
    (c) a fluid-impermeable baffle positioned adjacent to said second surface of said absorbent, said baffle and cover cooperating to enclose said absorbent; and
    (d) nonwoven means for retaining said absorbent article in frictional contact with said undergarment, said nonwoven means being secured to said baffle and having an external frictional surface with a Sheffield smoothness rating of greater than 400.

15. The absorbent article of claim 14 wherein said nonwoven means is a fibrous web.

16. The absorbent article of claim 15 wherein said fibrous web is secured to said baffle by an adhesive.

17. The absorbent article of claim 15 wherein said fibrous web is secured to said baffle by two-sided tape.

18. The absorbent article of claim 14 wherein said nonwoven means has a coefficient of friction of greater than about 2 and is skid-resistant.

19. An absorbent article designed to contact the perineum of a human body, said article comprising:
    (a) an absorbent having first and second surfaces;
    (b) a fluid-permeable cover positioned adjacent to said first surface of said absorbent;
    (c) a fluid-impermeable baffle positioned adjacent to said second surface of said absorbent, said baffle and cover cooperating to enclose said absorbent; and
    (d) nonwoven means for retaining said absorbent article in a desired position relative to said perineum, said nonwoven means being an elastomeric web secured to said baffle and having an external frictional surface with a Sheffield smoothness rating of greater than 400 and a coefficient of friction of greater than about 2.

20. An absorbent article designed to contact the perineum of a human body, said article comprising:
    (a) an absorbent having first and second surfaces;
    (b) a fluid-permeable cover positioned adjacent to said first surface of said absorbent;
    (c) a fluid-impermeable baffle positioned adjacent to said second surface of said absorbent, said baffle and cover cooperating to enclose said absorbent; and
    (d) nonwoven means for retaining said absorbent article in a desired position relative to said perineum, said nonwoven means being a fibrous elastomeric web secured to said baffle and having an external frictional surface with a Sheffield smoothness rating of greater than about 400.

21. The absorbent article of claim 20 wherein said nonwoven means is dry and non-tacky to the touch.

22. An absorbent article designed to contact the perineum of a human body, said article comprising:
(a) a fluid-permeable cover;
(b) a fluid-impermeable baffle;
(c) an absorbent positioned between and enclosed by said cover and said baffle to form a pad having a pair of outwardly extending wings; and
(d) fibrous nonwoven means for retaining said pad in a desired position relative to said perineum, said nonwoven means being secured to said baffle and having an external frictional surface with a Sheffield smoothness rating of greater than about 400.

23. The absorbent article of claim 22 wherein said nonwoven means is secured to at least a portion of one side of said wings.

24. The absorbent article of claim 22 wherein said nonwoven means is secured to both sides of said wings.

25. The absorbent article of claim 22 wherein said nonwoven means is secured to one of said wings.

26. A method of retaining an absorbent article in a desired position relative to the perineum of a human body, said absorbent article having a cover, a baffle, and an absorbent positioned between and enclosed by said cover and said baffle, and a nonwoven web secured to said baffle, said nonwoven web having an external frictional surface with a Sheffield smoothness rating of greater than about 400, said method comprising the steps of:
(a) placing said absorbent article adjacent to said human body with said cover contacting said perineum; and
(b) positioning an undergarment around said perineum; and
(c) contacting said undergarment with said frictional surface of said nonwoven web whereby said absorbent article is held stationary relative to said undergarment.

27. An absorbent article comprising:
(a) an absorbent having first and second surfaces;
(b) a fluid-permeable cover attached to said first surface of said absorbent; and
(c) a nonwoven, fluid-impermeable web attached to said second surface of said absorbent and cooperating with said cover to enclose said absorbent, said web having an external frictional surface with a Sheffield smoothness rating of greater than about 400.

* * * * *

UNITED STATES PATENT AND TRADEMARK OFFICE
CERTIFICATE OF CORRECTION

PATENT NO. : 5,011,480
DATED : April 30, 1991
INVENTOR(S) : Anthonette A. Gossens; Mary L. Schwer It is certified that error appears in the above-identified patent and that said Letters Patent is hereby corrected as shown below:

On the title page, Item[56] under Attorney, Agent, or Firm, delete "Conelly" and substitute therefor --Connelly--.

In the ABSTRACT, line 5, delete the word "hs" and substitute therefor --has--.

Signed and Sealed this

Twenty-sixth Day of October, 1993

*Attest:*

BRUCE LEHMAN

*Attesting Officer*     *Commissioner of Patents and Trademarks*